US00PP26792P3

(12) United States Plant Patent
Olesen

(10) Patent No.: US PP26,792 P3
(45) Date of Patent: Jun. 7, 2016

(54) SHRUB ROSE PLANT NAMED 'POULREN024'

(50) Latin Name: ***Rosa* hybrid**
Varietal Denomination: Poulren024

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 89 days.

(21) Appl. No.: 14/121,285

(22) Filed: Aug. 15, 2014

(65) Prior Publication Data

US 2016/0050800 P1 Feb. 18, 2016

(51) Int. Cl.
*A01H 5/00* (2006.01)

(52) U.S. Cl.
USPC ..... Plt./108

(58) Field of Classification Search
USPC ..... Plt./108
See application file for complete search history.

(56) References Cited

PUBLICATIONS

PLUTO Plant Variety Database Dec. 24, 2015. p. 1.*

* cited by examiner

*Primary Examiner* — Annette Para

(57) ABSTRACT

A new garden rose plant of the Shrub class which has abundant, red flowers and attractive foliage. This new and distinct variety has shown to be uniform and stable in the resulting generations from asexual propagation.

3 Drawing Sheets

Botanical designation: *Rosa* hybrid.
Variety denomination: 'Poulren024'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulren024', originated as a single seedling from the stated cross.

The new variety may be distinguished from its male pollen parent and female seed parent primarily by the following characteristics. The female seed parent has red flowers that are not fragrant, while the new variety has red flowers that are have strong perfume. The male pollen parent plan has an average growth height of 150 cm, while the new variety is 100 cm.

The objective of the hybridization of this rose variety was to create a new and distinct variety for garden use with unique qualities, such as:

1. Uniform and abundant red perfumed flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulren024' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulren024' was selected in the spring of 2007 by the inventor as a single plant from the progeny of the aforementioned hybridization.

Asexual reproduction of 'Poulren024' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulren024' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren024'.

Specifically illustrated in FIG. 1 are open flowers, flower buds, and flowers in parts.

Figure 1:
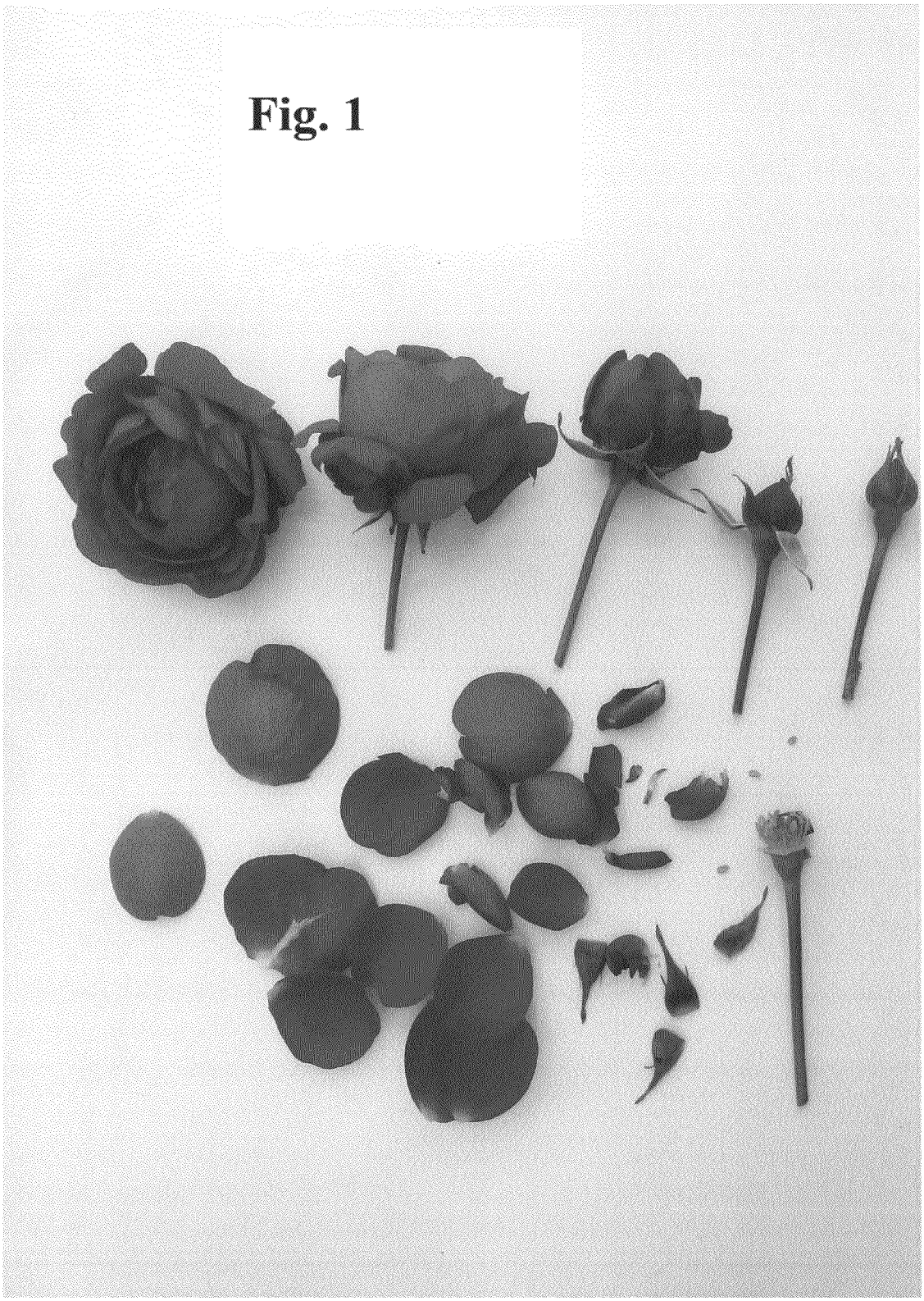
Figure 2:
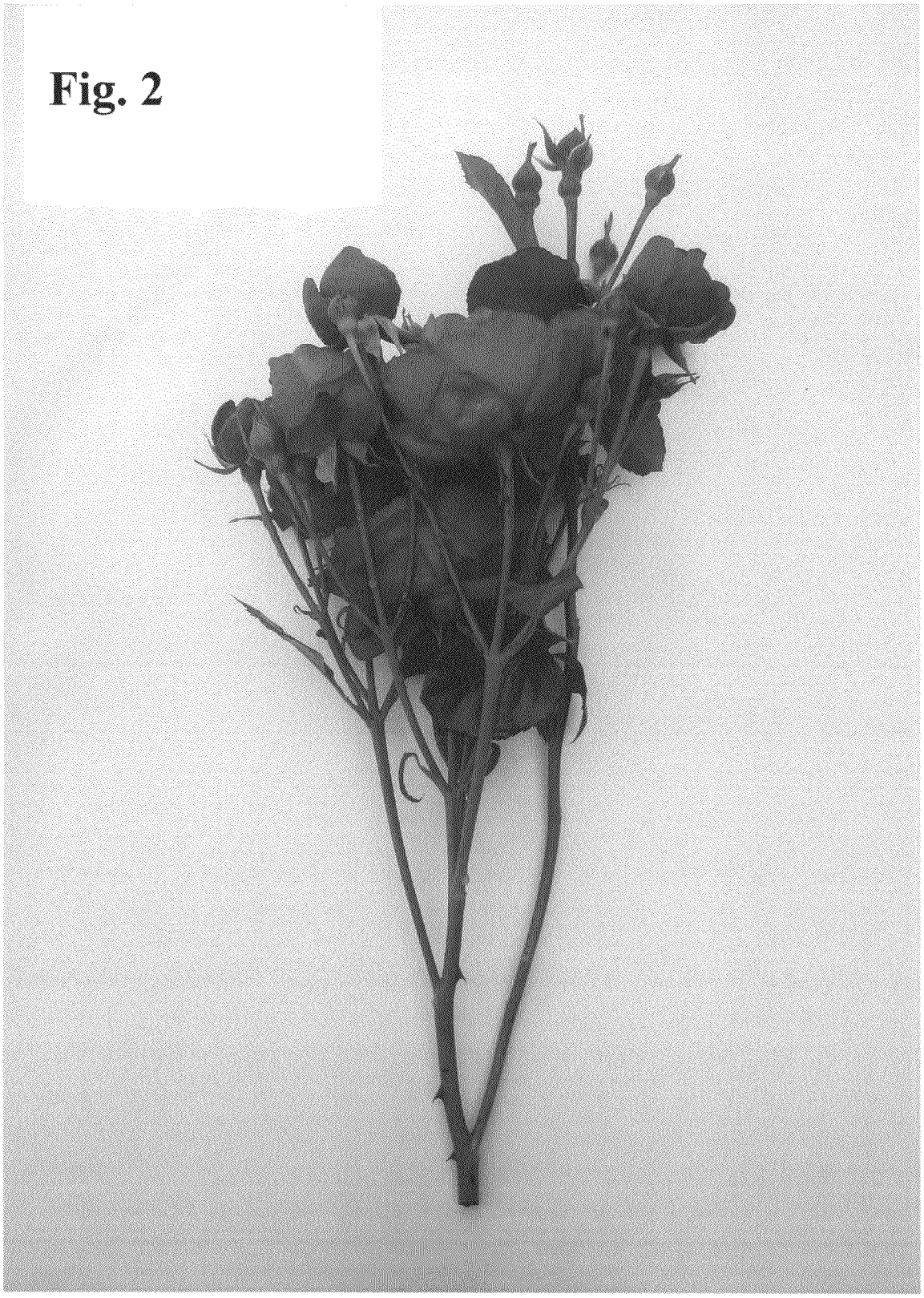
FIG. 2 shows a flowering branch.
Figure 3:
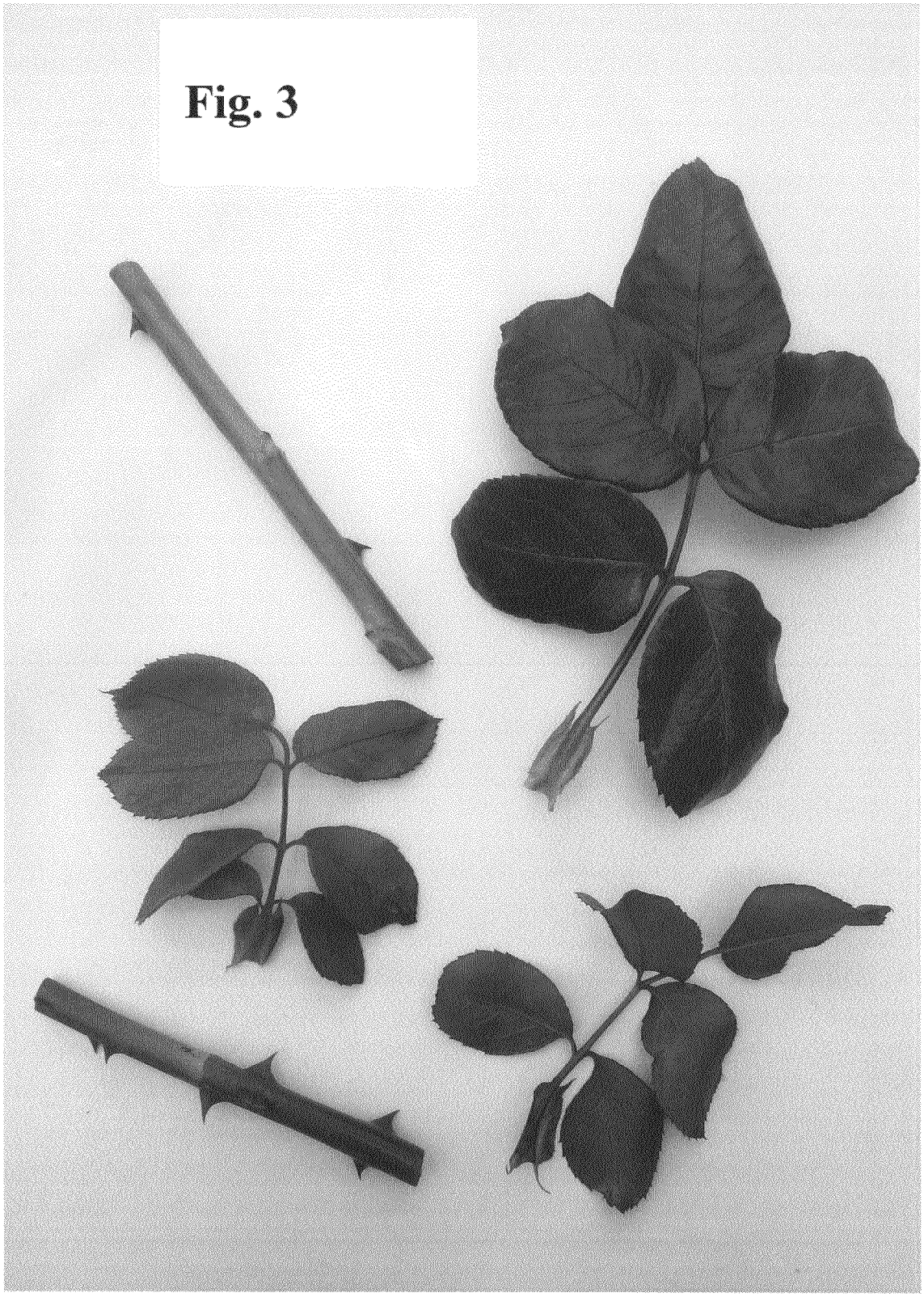
FIG. 3 shows leaves and stems.

Plants shown are 2 years of age.

DETAILED DESCRIPTION OF THE VARIETY

The following is a description of 'Poulren024', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulisab', U.S. Plant Pat. No. 12,825 are compared to 'Poulren024' in Chart 1.

CHART 1

| | 'Poulren024' | 'Poulisab' |
|---|---|---|
| Petal Count | 40 | 55-70 |
| Flower Diameter | 75 mm | 80 mm |
| General Tonality of Flower Color | Red Group 46A | Red Group 46A |

Flower and Flower Bud

Blooming habit: Continuous.

Flower bud:

*Size*.—Upon opening, 30 mm in length from base of receptacle to end of bud. Bud diameter is 15 mm.

*Bud form*.—Ovoid.

*Bud color*.—As sepals divide petals are Greyed-Purple Group 187A and Red Group 46A.

*Sepal inner surface*.—Color: Yellow-Green Group 145A. Surface: Lightly pubescent.

*Sepal outer surface*.—Color: Yellow-Green Group 144A with intonations of Greyed-Purple Group 187B. Texture: Smooth.

*Sepal shape*.—Apex: Cirrhose. Base: Flat at union with receptacle.

*Sepal margin*.—Margins have weal foliaceous appendages on three of the five sepals.

*Sepal size*.—28 mm long, 15 mm wide.

*Receptacle*.—Texture: Smooth. Size: 9 mm in height, 8 mm wide. Color: Yellow-Green Group 144A with intonations of Greyed-Purple Group 187B. Shape: Campanulate.

*Pedicel*.—Surface: Smooth. Length: About 45 mm. Diameter: 3 mm on average. Color: Yellow-Green Group 144A with intonations of Greyed-Purple Group 183B. Strength: Strong.

*Peduncle*.—Length: 8 to 20 cm. Diameter: About 3 mm. Color: Yellow-Green Group 144A. Texture: Large prickles.

Flower bud development: Flower buds are borne in clusters of 3 to 15 flower buds per stem.

Flower bloom:

*Fragrance*.—Strong perfume.

*Duration*.—The blooms have a duration on the plant of approximately 7 to 10 days. Petals fall cleanly away from plant after flowers have fully matured.

*Size*.—Flower diameter is 75 mm when open. Flower depth is 35 mm.

*Flower shape*.—Quartered-rosette, very double, with many overlapping petals packed into quarter sections.

*Shape of flower, side view*.—The upper portion is flat. The lower portion is concave.

Petalage: Under normal conditions, flowers have 40 petals total, 4 to 5 of which are petaloids.

General tonality of flower: Open flowers are Red Group 46A.

Petal color:

*Upon opening, outer petals*.—Upper surface: Red Group 46B, with occasional streak of White Group 155A. Lower surface: Red Group 46A.

*Upon opening, inner petals*.—Upper surface: Red Group 46B. Lower surface: Red Group 46A.

*Basal petal spots*.—Upon opening, no distinctive coloration at the petal base observed.

*After opening, outer petals*.—Upper surface: Red Group 46B, with occasional streak of White Group 155A. Lower surface: Red Group 46A.

*After opening, inner petals*.—Upper surface: Red Group 46B. Lower surface: Red Group 46A.

*Basal petal spots*.—After opening, no distinctive coloration at the petal base observed.

Petals:

*Petal reflex*.—Flat.

*Margin*.—Entire and uniform. No undulations.

*Shape*.—Generally rounded. Apex shape: Rounded. Base shape: Rounded.

*Size*.—40 mm (l)×45 mm (w).

*Texture*.—Smooth.

*Thickness*.—Average.

Petaloids:

*Size*.—15 mm (l) by 12 mm (w).

*Quantity*.—4 to 5.

*Shape*.—Elliptical, with an acute apex and base.

*Color*.—Upper surface is Red Group 46B, with occasional streak of White Group 155A. Lower surface is Red Group 46A.

Reproductive flower parts:

*Pollen*.—None observed.

*Anthers*.—Size: 2 mm in length. Color: Yellow-Orange Group 22B. Quantity: 50 on average.

*Filaments*.—Color: Green-Yellow Group 1D. Length: 5 mm.

*Pistils*.—Length: 5 mm. Quantity: 25 on average.

*Stigmas*.—Color: Greyed-Yellow Group 160A.

*Styles*.—Color: Red Group 46D.

*Location of stigmas*.—Level in location relative to the length of the filaments and the height of the anthers.

*Hips*.—None Observed.

Plant

Plant growth: Upright, bushy. Plants are 100 cm in height, and 80 cm wide.

Stems:

*Color*.—Juvenile growth: Yellow-Green Group 147C with strong intonations of Greyed-Purple Group 187B. Mature growth: Yellow-Green Group 147B.

*Length*.—On average, canes are 70 cm from the base of the plant to the flowering portion.

*Diameter*.—About 10 mm.

*Internodes*.—On mature canes about 30 mm between nodes.

*Surface texture*.—Young wood: Smooth. Older wood: Smooth.

Long prickles:

*Incidence*.—8 prickles per 10 cm of stem.

*Size*.—Average length of prickles on mature stems is 6 mm.

*Shape*.—Upper portion is linear. Lower portion is concave.

*Color*.—Juvenile prickles: Greyed-Purple Group 187B. Mature prickles: Greyed-Orange Group 173B.

Plant foliage:

*Compound leaf*.—120 mm (l)×100 mm (w).

*Quantity*.—About 3 leaves per 10 cm of stem on average.

*Leaf bearing angle to the stem*.—45 degrees.

*Color of juvenile foliage*.—Upper side: Yellow-Green Group 147B. Lower side: Yellow-Green Group 147C. Anthocyanin: Strong, Greyed-Purple Group 187A.

*Color of mature foliage*.—Upper side: Yellow-Green Group 147A. Lower side: Yellow-Green Group 147B.

Plant leaves and leaflets:

*Stipules*.—Size: 15 mm long, 3 mm wide. Quantity: 2 per compound leaf. Shape: Linear, slightly broad based with outward extending apices. Margins: Finely serrated. Color: Yellow-Green Group 144C.

*Petiole*.—Length: 20 mm. Diameter: 2 mm.

*Upper surface*.—Color: Yellow-Green Group 144A with light intonations of Greyed-Red Group 181C.

*Lower surface*.—Color: Yellow-Green Group 144B.

*Rachis*.—Length: 45 mm. Upper surface color: Yellow-Green Group 144A.

*Lower surface*.—Color: Yellow-Green Group 144B. Observations: Small prickles.

*Leaflet*.—Quantity: Normally 5 leaflets. Margins: Serrated. Size: On average terminal leaflets are 55 mm long, 45 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Shrub rose class named 'Poulren024', substantially as illustrated and described herein, due to its abundant red flowers, disease resistance, and extended period of bloom.

* * * * *